United States Patent [19]

Aoda et al.

[11] 4,344,968

[45] Aug. 17, 1982

[54] PHARMACEUTICAL VEHICLE

[75] Inventors: Yukio Aoda, Tokyo; Hiroshi Ninomiya, Sayama; Kooichi Yoshida, Soka; Osamu Koyanagi, Yono, all of Japan

[73] Assignee: Nippon Kayaku Kabushiki Kaisha, Tokyo, Japan

[21] Appl. No.: 101,707

[22] Filed: Dec. 10, 1979

[30] Foreign Application Priority Data

Dec. 9, 1978 [JP] Japan .................. 53-152221

[51] Int. Cl.³ .............. A61K 9/02; A61K 9/22; A61K 9/26; A61K 31/78
[52] U.S. Cl. .................. 424/365; 424/19; 424/22; 424/81; 424/358; 128/271; 424/365;81
[58] Field of Search ........................ 128/271

[56] References Cited

U.S. PATENT DOCUMENTS

| | | | |
|---|---|---|---|
| 2,584,166 | 2/52 | Stevenson et al. | 128/271 |
| 2,696,456 | 12/54 | Hotterick | 128/271 |
| 2,918,404 | 12/69 | Monds et al. | 128/271 |
| 3,440,320 | 4/69 | Sacklor | 128/271 |
| 3,776,001 | 12/73 | Hanke | 128/271 |
| 3,875,300 | 4/75 | Homm et al. | 128/271 |
| 4,151,274 | 4/79 | Schluetor et al. | 128/271 |

FOREIGN PATENT DOCUMENTS

| | | | |
|---|---|---|---|
| 212775 | 1/1957 | Australia | 128/271 |
| 647439 | 5/1964 | Belgium | 128/271 |
| 44-11675 | 5/1969 | Japan . | |
| 54-26325 | 2/1979 | Japan . | |
| 54-157820 | 12/1979 | Japan . | |
| 837451 | 6/1960 | United Kingdom . | |
| 931147 | 7/1963 | United Kingdom . | |
| 1552521 | 9/1979 | United Kingdom . | |

OTHER PUBLICATIONS

Anschol et al., Chap. 8, "Suppositories", pp. 245–273 in Lachman et al. (ED), The Theory and Practice of Industrial Pharmacy, 2nd Ed., (1976), Lea & Febiger, Phila., Pa.
Chem. Abstr. 92, #220693t (1980) of Jpn. Kokai Tokkyo Kobo 79157820, 13 Dec. 1979, Layered Suppository Base Compositions.
Chem. Abstr. 90, #210156g (1979) of Jpn. Kokai Tokkyo Kobo 7926325, 27 Feb. 1979, Suppositories.
Chem. Abstr. 71, #94739p (1969) of Japan, 69 11, 675, Waxy Compns. for Use as Ointment or Suppositories.

*Primary Examiner*—Shep K. Rose
*Attorney, Agent, or Firm*—Henry C. Nields

[57] ABSTRACT

Disclosed is a pharmaceutical vehicle comprising (a) a fatty acid glyceride having a melting point higher than 37° C., (b) a water-soluble, low viscous and non-irritating organic substance having a particle size smaller than 28 mesh and a viscosity lower than 300 cps as measured with respect to a 2% aqueous solution, (c) an organic polymeric substance having a particle size smaller than 28 mesh, which is capable of being swollen on contact with water, and (d) a water-soluble surface active agent.

5 Claims, 1 Drawing Figure

PHARMACEUTICAL VEHICLE

BACKGROUND OF THE INVENTION

1. Field of the Invention

The present invention relates to a pharmaceutical vehicle. More particularly, the present invention relates to a pharmaceutical vehicle excellent in the property of gradually releasing an active ingredient.

2. Description of the Prior Art

Various gradually releasing pharmaceutical compositions have been known, but most of them are used for oral administration and gradually releasing suppository compositions have hardly been known.

Recently, various attempts have been made to cure tumors by applying suppositories containing effective carcinostatic ingredients to the rectum, the uterus cervix, the vagina, the urethra and the like to allow the effective ingredients to act on the affected parts for a long time. For example, for remedy of uterine cancer, the effective ingredient is applied to the affected part once a day. Furthermore, in case of cancer of the rectus, it is necessary to apply the effective ingredient once a day because evacuation is ordinarily made once a day. Thus, suppositories of carcinostatic agents are ordinarily applied once a day. Therefore, development of a pharmaceutical vehicle for such suppositories capable of releasing the effective ingredient in about 24 hours has been desired.

Suppositories comprising a fatty acid glyceride as the vehicle are known. Since these suppositories are arranged so that the vehicle is molten by the body temperature to release the effective ingredient, a fatty acid glyceride having a melting point lower than the body temperature (37° C.) is used as the vehicle. Therefore, in scores of minutes after application of these suppositories, the vehicle is molten and the effective ingredient is released in a relatively short time. In short, these suppositories have not a property of gradually releasing the effective ingradient. Furthermore, when the effective ingredient has to be included at a high concentration, the area around the affected part becomes inflamed.

Suppositories comprising a carboxyvinyl polymer as the vehicle are known as gradually releasing suppositories. These suppositories, however, are defective in that the speed of releasing the effective ingredient is too low or the effective ingredient is not sufficiently released.

SUMMARY OF THE INVENTION

We made researches with a view to developing a pharmaceutical vehicle for a suppository, which can release an active ingredient uniformly over a period of several to about 24 hours and can release the active ingredient as completely as possible during this period. As a result, it was found that when a fatty acid glyceride having a melting period higher than 37° C., which has not been used for suppositories, is mixed with a water-soluble surface active agent, a water-soluble, low viscous and non-irritating organic substance and a water-swelling polymeric compound and the resulting composition is used as a suppository vehicle, the above-mentioned object can be attained. Based on this finding, we have now completed the present invention.

More specifically, in accordance with the present invention, there is provided a pharmaceutical vehicle comprising (a) a fatty acid glyceride having a melting point higher than 37° C., (b) a water-soluble, low viscous and non-irritating organic substance having a particle size smaller than 28 mesh and a viscosity lower than 300 cps as measured with respect to a 2% aqueous solution, (c) an organic polymeric substance having a particle size smaller than 28 mesh, which is capable of being swollen on contact with water, and (d) a water-soluble surface active agent.

This pharmaceutical vehicle of the present invention is characterized in that in Ringer's solution, the vehicle is gradually swollen with the lapse of time and is gradually cracked and disintegrated, and therefore, in a pharmaceutical composition comprising an effective ingredient incorporated in this vehicle, the effective ingredient can be gradually released uniformly and sufficiently over a period of several to about 24 hours. Furthermore, in the pharmaceutical vehicle of the present invention, the effective ingredient releasing time can be freely controlled within a range of from several hours to several days by adjusting the amounts of the respective components appropriately.

DETAILED DESCRIPTION OF THE PREFERRED EMBODIMENTS

Figure 1:
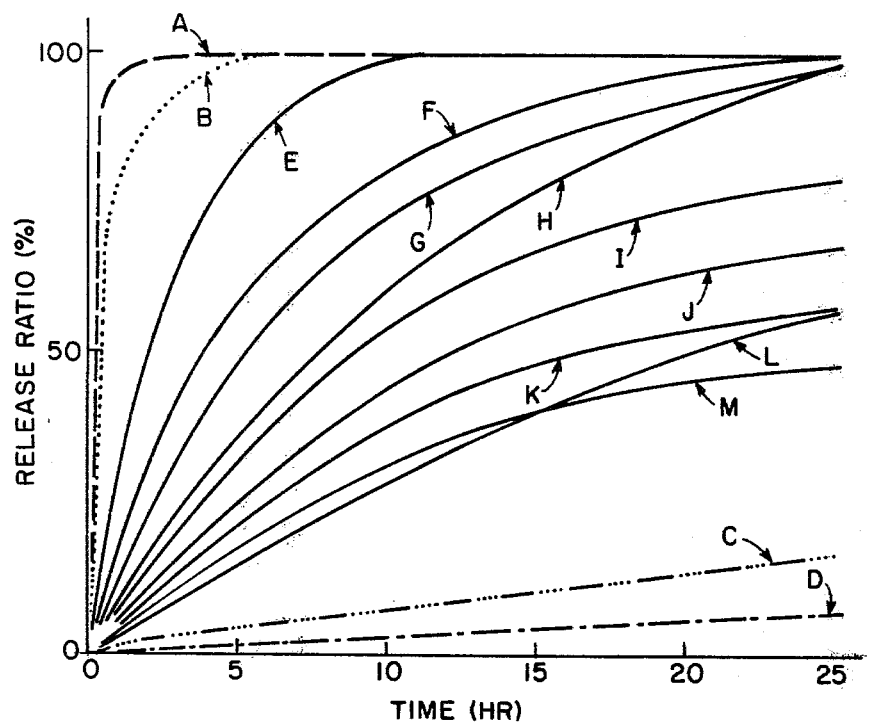
FIG. 1 is a diagram illustrating the relation between the release ratio of the effective ingredient and the time elapsed, observed in pharmaceutical vehicles of the present invention and comparative pharmaceutical vehicles.

The pharmaceutical vehicle of the present invention comprises as indispensable components (a) a fatty acid glyceride having a melting point higher than 37° C., (b) a water-soluble, low viscous and non-irritating organic substance having a particle size smaller than 28 mesh and a viscosity lower than 300 cps as measured with respect to a 2% aqueous solution, (c) an organic polymeric substance having a particle size smaller than 28 mesh, which is capable of being swollen on contact with water, and (c) a water-soluble surface active agent. These indispensable components will now be described.

As the fatty acid glyceride that is used in the present invention, there can be mentioned, for example, monoglycerides, diglycerides and triglycerides of vegetable fatty acids (usually, mixtures of fatty acids having the carbon atom number of 10 to 18) obtained from coconut oil, olive oil and the like, and mixtures of these glycerides. These glycerides should have a melting point higher than 37° C., and it is preferred that the melting point be not higher than 42° C. For example, a mixture of Witepsol ® H15 (manufactured by Dynamic Nobel Chemicals Co. Ltd.) or Suppocire ® AM (manufactured by Gattefosse Co., Ltd.) obtained from coconut oil and having a melting point of 34.6° C. and Witepsol ® E85 or Suppocire ® DM having a melting point of 42° C. may be used. The fatty acid glyceride is used in an amount of 10 to 95% by weight, preferably 40 to 80% by weight, based on the total pharmaceutical vehicle.

As the water-soluble, low viscous and non-irritating organic substance, there can be used, for example, amino acids, saccharides and low viscous, water-soluble polymeric substances. As the amino acid, there can be mentioned, for example, alanine, glycine, phenylalanine, leucine, isoleucine, valine, lysine, proline and serine. As the saccharide, there can be mentioned, for example, glucose, maltose, mannitol, fructose, galactose, lactose, dextrose, xylitol, sorbitol, mannose and sucrose. As the viscous, water-soluble polymeric substance, there can be mentioned, for example, polymeric substances derived from natural products, such as dextrin, dextran, xylan, carragheenin, mannan, an alginic acid ester or propylene glycol, soluble starch, gum arabic, tragacanth gum, α-cyclodextrin, β-cyclodextrin, galactan and inulin. These substances are used for facilitating elution of the effective ingredient from the pharmaceutical vehicle. The water solubility of these substances is at least 5%, preferably 10 to 30%, and the viscosity is lower than 300 cps as measured with respect to a 2% aqueous solution. The particle size of these substances is smaller than 28 mesh (Tyler standard), preferably smaller than 200 mesh. These substances may be used singly or in the form of a mixture of two or more of them. These substances are used in an amount of 5 to 80% by weight, preferably 10 to 50% by weight, based on the total pharmaceutical vehicle.

As the organic polymeric substance capable of being swollen on contact with water, there can be mentioned, for example, carboxyvinyl polymers such as Carbopol ® (manufactured by B. F. Goodrich Chemical Co., Ltd) and polyacrylic acid, metal salts thereof, such as sodium and calcium salts, polyethylene oxide, gelatin, chondroitin sulfate, amylose, microcrystalline cellulose, carboxymethyl cellulose, metal salts thereof such as sodium and calcium salts, methyl cellulose and hydroxypropylmethyl cellulose. Sodium polyacrylate is most preferred because it has a highest swelling capacity. These organic polymeric substances should have a particle size of smaller than 28 mesh (Tyler standard), preferably smaller than 200 mesh. These organic polymeric substances may be used singly or in the form of a mixture of two or more of them. If the ratio of a polymeric substance having a high water solubility, such as sodium (polyacrylate), is too high, release of the effective ingredient is remarkably retarded because of a high viscosity thereof. If the ratio of a polymeric substance low in the water solubility, such as microcrystalline cellulose, is increased, the disintegration speed of the vehicle becomes too high and the gradually releasing characteristic is lost.

Such water-swelling organic substance is used in an amount of 0.1 to 10% by weight, preferably 0.2 to 2% by weight, based on the total pharmaceutical vehicle.

As the water-soluble surface active agent, there can be mentioned, for example, polyoxyethylene sorbitan monooleate such as Tween ® 80 (manufactured by Nikko Chemical Co., Ltd.) and polyoxyethylene sorbitan-hydrogenated castor oil derivatives such as HCO ® 60 (manufactured by Nikko Chemical Co., Ltd.). The water-soluble surface active agent is used in an amount of 0.001 to 10% by weight, preferably 0.05 to 5% by weight, based on the total pharmaceutical vehicle.

Various pharmaceutical compositions differing in the speed of release the effective ingredient can be obtained by using the pharmaceutical vehicle of the present invention while appropriately adjusting the mixing ratios of the respective components. Especially, the release speed of the effective ingredient can easily be controlled by adjusting the mixing ratio of the water-soluble, low viscous and non-irritating organic substance.

The preparation of the pharmaceutical vehicle of the present invention will now be described.

The fatty acid glyceride having a melting point higher than 37° C. is heated and molten, and the water-soluble, low viscous organic substance, the organic polymeric substance capable of being swollen on contact with water and the water-soluble surface active agent are incorporated in and kneaded with the melt of the fatty acid glyceride.

The pharmaceutical vehicle of the present invention which is prepared according to the above process is especially suitable as a vehicle for a suppository, but it can also be used as a vehicle for a medicine for oral administration. A gradually releasing suppository or medicine for oral administration may be prepared by incorporating an effective ingredient into the pharmaceutical vehicle of the present invention, optionally with taste and smell correctives in case of the medicine for oral administration, and forming the resulting composition into an appropriate shape.

Any of effective ingredients that should be formed into gradually releasing pharmaceutical compositions or that are preferably formed into gradually releasing pharmaceutical compositions can be used. For example, there can be mentioned antipyretic, analgesic and anti-inflammatory agents such as acetyl salicylate, aminopyrine, indomethacin, oxyphenbutazone, sulpyrine, pyrabital, sodium dichlorofenac and ibuprophene, antihistamics such as d-maleic acid chloropheniramine, triprolidine hydrochloride, promethazine, thonzylamine hydrochloride and clemastin fumarate, antibiotics such as penicillins, cephalosporins, tetracyclines, erythromycin, josamycin and spiramycin, carcinostatic agents such as bleomycins such as disclosed in U.S. Pat. Nos. 3,681,491, 3,846,400, Ger. Offen. No. 2828933, futraful, mitomycin and 5FU, local anesthetics such as procaine hydrochloride, T-Cain, dibucaine and lidocaine, anticeptic agents such as fradiomycin sulfate, gentamicin sulfate and sulfonamides, vitamins such as ascorbic acid, and hormones such as testosterone and progesterone. The amount of the effective ingredient differs depending on the kind of the effective ingredient. For example, hormones are incorporated in amounts of 0.0001%, vitamins are incorporated in amounts of about 50% and bleomycins are incorporated in amounts of 0.25 to 3%, based on the pharmaceutical vehicle of the present invention.

Pharmaceutical compositions formed by using the pharmaceutical vehicle of the present invention may be formed into gradually releasing suppositories having a shape suitable for the part to be applied, for example, a tablet-like shape, a pellet-like shape, a spindle-like shape, a pencil-like shape or a spherical shape. Further, these pharmaceutical compositions may be formed into gradually releasing drugs suitable for oral administration according to customary techniques adopted in the art of pharmaceutics. Moreover, these gradually releasing pharmaceutical compositions may be used in combination with instantaneously releasing pharmaceutical compositions.

The process for the preparation of the pharmaceutical vehicle of the present invention will now be described with reference to the following Examples.

EXAMPLE 1

A mixture of 26.1 g of Witepsol H15 and 39.2 g of Witepsol E85 was heated and molten at about 50° C. A part of the melt was mixed and sufficiently kneaded with 30 g of powdered glycine passed through a 200-mesh sieve, 0.5 g of sodium polyacrylate passed through a 250-mesh sieve and 2.5 g of Tween 80, and the kneaded mixture was combined with the remainder of the melt. The mixture was sufficiently and homogeneously blended and kneaded at a temperature maintained at about 50° C. to form a pharmaceutical vehicle.

EXAMPLE 2

A mixture of 20.4 g of Suppocire AM and 35.6 g of Suppocire DM was heated and molten at about 50° C., and a part of the melt was mixed and sufficiently kneaded with 20 g of mannitol passed through a 250-mesh sieve, 2.0 g of gelatin passed through a 200-mesh sieve and 2.0 g of a polyoxyethylene-hydrogenated castor oil derivative (HCO-60). The mixture was combined with the remainder of the melt, and the resulting mixture was sufficiently and homogeneously blended and kneaded to form a vehicle.

The process for the preparation of pharmaceutical compositions by using the pharmaceutical vehicle of the present invention will now be described with reference to the following Examples.

EXAMPLE 3

To the whole amount of the vehicle prepared in Example 1 was added 1.7 g (activity factor of about 3 g) of powdery bleomycin hydrochloride while the vehicle was maintained at 50° C., and after sufficient mixing, the temperature was lowered to 45° C., and the mixture was placed in spindle-shaped molds so that 1 g of the mixture was packed in each mold and the mixture was cooled and solidified. Thus, there were obtained drugs, each containing bleomycin hydrochloride in an activity factor of about 30 mg.

EXAMPLE 4

A mixture of 26.1 g of Witepsol H15 and 39.2 g of Witepsol E85 was heated and molten at about 50° C. A part of the molten mixture was mixed and sufficiently kneaded with 30 g of powdered glycine passed through a 200-mesh sieve, 0.5 g of sodium polyacrylate passed through a 250-mesh sieve, 2.5 g of Tween 80 and 2 g (activity factor of about 2 g) of 3[(S)-1'-phenylethylamino]-propylaminobleomycin powder, and the mixture was combined with the remainder of the melt. The resulting mixture was sufficiently and homogeneously blended and kneaded while the mixture was maintained at about 50° C. Then, the temperature was lowered to about 45° C. and the mixture was placed in bullet-shaped molds so that 1.0 g of the mixture was packed in each mold. The mixture was cooled and solidified in these molds to obtain gradually releasing drugs, each containing the effective ingredient in an activity factor of about 20 mg.

EXAMPLE 5

A mixture of 20.4 g of Suppocire AM and 35.6 g of Suppocire DM was heated and molten at about 50° C. A part of the melt was sufficiently and homogeneously glended and kneaded with 20 g of mannitol passed through a 250-mesh sieve, 2.0 g of gelatin passed through a 200-mesh sieve, 2.0 g of a polyoxyethylene-hydrogenated castor oil derivative (HCO-60) and 20 g of erythromycin. Then, the temperature was lowered to about 45° C., and the mixture was placed in spherical molds so that 1 g of the mixture was packed in each mold. The mixture was cooled and solidified in these molds to obtain gradually releasing drugs, each containing 200 mg of erythromycin.

It will now be clarified that the pharmaceutical vehicle of the present invention has an appropriate speed of gradually releasing the effective ingredient and this release speed can be freely controlled, with reference to the following Experiment.

EXPERIMENT (1) Preparation of Samples:

Bleomycin hydrochloride was incorporated as the effective ingredient in an activity factor of 30 mg into a vehicle prepared in the same manner as described in Example 1 according to a recipe shown in Table 1, and the total amount was adjusted to 1000 mg. The mixture was molded into spindles having a bottom diameter of 10 mm and a height of 16 mm. Thus, there were prepared samples E to M according to the present invention and comparative samples A to D, as indicated in Table 1.

TABLE 1

| | | | Fatty Acid Glyceride | | | |
|---|---|---|---|---|---|---|
| Recipe | Witepsol ® H15 (a) or Suppocire ® AM (b) | Witepsol ® E85 (a) or Suppocire ® DM (b) | Melting Point (°C.) | Lowly Viscous Water-Soluble Substance | Water-Swelling Polymeric Substance | Water-Soluble Surface Active Agent |
| A | a. 100.0 | — | 34.6 | — | — | — |
| B | a. 80.0 | a. 20.0 | 36.6 | — | — | — |
| C | a. 70.0 | a. 30.0 | 37.8 | — | — | — |
| D | a. 60.0 | a. 40.1 | 38.8 | — | — | — |
| E | a. 38.1 | a. 16.4 | 37.8 | glycine 40 | PANA* 2.0 | Tween 80 3.5 |
| F | a. 36.6 | a. 24.4 | 38.8 | mannitol 35 | CMC-Ca** 1.5 | Tween 80 2.5 |
| G | a. 26.8 | a. 40.2 | 40.5 | glycine 30 | PANA 0.5 | Tween 80 2.5 |
| H | a. 45.9 | a. 30.6 | 38.8 | maltose 20 | gelatin 1.5 | HCO 60 2.0 |
| I | a. 45.9 | a 30.6 | 38.8 | glycine 20 | PANA 1.0 | Tween 80 2.5 |
| J | b. 23.1 | b. 53.9 | 41.6 | alanine 20 | PANA 0.5 | Tween 80 2.5 |
| K | b. 30.4 | b. 45.6 | 40.5 | dextrin 20 | gelatin 2.0 | Tween 80 2.0 |
| L | b. 31.4 | b. 47.1 | 40.5 | mannitol 20 | PANA 0.5 | Tween 80 1.0 |
| M | b. 48.9 | b. 32.6 | 38.8 | glycine 15 | microcry-stalline cellulose | HCO 60 3.0 |

TABLE 1-continued

| Recipe | Fatty Acid Glyceride | | Melting Point (°C.) | Lowly Viscous Water-Soluble Substance | Water-Swelling Polymeric Substance | Water-Soluble Surface Active Agent |
|---|---|---|---|---|---|---|
| | Witepsol® H15 (a) or Suppocire® AM (b) | Witepsol® E85 (a) or Suppocire® DM (b) | | | | |
| | | | | | 0.5 | |

Note
*PANA: sodium polyacrylate
**CMC-Ca: calcium carboxymethyl cellulose (2) Test Procedures:

In a test tube having a diameter of 17 mm was charged 10 ml of Ringer's solution (Japanese Pharmacopoeia). Twelve test tubes were used for each sample. The test tubes were dipped in a thermostat tank maintained at 37° C. and one gradually releasing drug sample prepared above, which was wrapped with gauze, was dipped in Ringer's solution in the first test tube and the test tube was allowed to stand still. Then, at intervals of 2 hours, samples were charged in the fresh test tubes successively. At predetermined intervals, the amount of bleomycin hydrochloride being related in Ringer's solution was determined by measuring the absorbance at a wave length of 292.5 nm.

(3) Results:

The obtained results are shown in FIG. 1. From these results, it will readily be understood that in comparative samples A and B formed by using the fatty acid glyceride having a melting point lower than 37° C., about 50% of the effective ingredient is released within 30 minutes from the start of the experiment and in comparative samples C and D formed by using only the fatty acid glyceride having a melting point higher than 37° C., only 17% (in sample C) or 7% (sample D) of the effective ingredient is released even after 24 hours from the start of the experiment. In contrast, as will be apparent from the results shown in FIG. 1, when the pharmaceutical vehicle of the present invention is used, the effective ingredient is ordinarily dissolved out substantially completely in about 24 hours (see samples F, G and H) and this released time can be controlled within a range of from about 10 hours (see sample E) to a time longer than 24 hours (samples I to M). Thus, it will readily be understood that the release speed of the effective ingredient can be freely controlled by appropriately adjusting the mixing ratios of the components of the pharmaceutical vehicle of the present invention.

What is claimed is:

1. A pharmaceutical vehicle comprising (a) a fatty acid glyceride having a melting point higher than 37° C. and being used in an amount of 40 to 80% by weight, (b) (b) one member selected from the group consisting of alamine, glycine, phenylalanine, leucine, isoleucine, valine, lysine, proline, serine, glucose, maltose, mannitol, fructose, galactose, lactose, dextrose, xylitol, sorbitol, mannose, sucrose, dextrin, dextran, xylann, carragheenin, mannan, an alginic acid ester of propyleneglycol, soluble starch, gum arabic, tragacamth gum, α-cyclodextrin, β-cyclodextrin, galactan and inulin: said substances having a particle size smaller than 28 mesh and being used in an amount of 10 to 50% by weight, (c) sodium polyacrylate having a particle size smaller than 28 mesh and being used in an amount of 0.2 to 2% by weight, and (d) a water-soluble surface active agent being used in an amount of 0.05 to 5% by weight.

2. A pharmaceutical vehicle as set forth in claim 1 wherein the fatty acid glyceride is at least one member selected from the group consisting of monoglycerides, diglycerides and triglycerides of vegetable fatty acids.

3. A pharmaceutical vehicle as set forth in claim 1 wherein the water-soluble surface active agent is at least one member selected from polyoxyethylene sorbitan monooleate and polyoxyethylene sorbitan-hydrogenated castor oil derivatives.

4. A gradually releasing pharmaceutical composition comprising (a) a fatty acid glyceride having a melting point higher than 37° C. and being used in an amount of 40 to 80% by weight, (b) one member selected from the group consisting of alamine, glycine, phenylalanine, leucine, isoleucine, valine, lysine, proline, serine, glucose, maltose, mannitol, fructose, galactose, lactose, dextrose, xylitol, sorbitol, mannose, sucrose, dextrin, dextran, xylan, carragheenin, mannan, an alginic acid ester of propyleneglycol, soluble starch, gum arabic, tragacamth gum, α-cyclodextrin, β-cyclodextrin, galactan and inulin: said substances having a particle size smaller than 28 mesh, (c) sodium polyacrylate having a particle size smaller than 28 mesh, and being used in an amount of 0.2 to 2% by weight, (d) a water-soluble surface active agent, being used in an amount of 0.05 to 5% by weight, and (e) an effective ingredient being used in an amount of 0.0001 to 50%, based on the total weight of the said (a), (b), (c) and (d).

5. A gradually releasing pharmaceutical composition as set forth in claim 4 wherein (a) is a glyceride of a vegetable fatty acid obtained from coconut oil, (b) is glycine, the water-soluble surface active agent (d) is polyoxyethylene sorbitan monooleate and (e) is bleomycins being used in an amount of 0.25 to 3%.

* * * * *